(12) United States Patent
Ghosh

(10) Patent No.: US 7,642,045 B2
(45) Date of Patent: Jan. 5, 2010

(54) ANTIBODIES TO PROTEIN MARKERS ASSOCIATED WITH BONE MARROW STEM CELL DIFFERENTIATION INTO EARLY PROGENITOR DENDRITIC CELLS

(76) Inventor: Swapan K. Ghosh, 120 Phoenix St., Terre Haute, IN (US) 47803

(*) Notice: Subject to any disclaimer, the term of this patent is extended or adjusted under 35 U.S.C. 154(b) by 0 days.

(21) Appl. No.: 11/283,005

(22) Filed: Nov. 18, 2005

(65) Prior Publication Data
US 2007/0269867 A1 Nov. 22, 2007

Related U.S. Application Data

(60) Provisional application No. 60/629,110, filed on Nov. 18, 2004.

(51) Int. Cl.
A01N 1/02 (2006.01)
C12N 5/00 (2006.01)
C07K 16/00 (2006.01)
C07K 5/00 (2006.01)
A61K 39/38 (2006.01)
A61K 39/395 (2006.01)

(52) U.S. Cl. .......... 435/2; 435/377; 530/387.1; 530/300; 424/184.1; 424/153.1

(58) Field of Classification Search .......... None
See application file for complete search history.

(56) References Cited

U.S. PATENT DOCUMENTS 6,479,286 B1 11/2002 Nelson et al.

2003/0104569 A1 6/2003 Oritani et al.
2003/0194704 A1* 10/2003 Penn et al. ............ 435/6
2003/0194803 A1 10/2003 Mellor et al.
2004/0171036 A1* 9/2004 Wang ............ 435/6
2007/0048740 A1* 3/2007 Isogai et al. ............ 435/6

OTHER PUBLICATIONS

Gerez et al. Mol Biol Cell 11: 2201-2211, 2000.*
Al-Shaibi and Ghosh, Biochim Biophys Res Comm 321: 26-30, 2004.*
Dakic et al Leuk Lymph 44: 1469-1475, 2003.*
Wu et al., Immunol Rev. 26: 741-750, 2007.*
Wan et al. Cell Mol Immunol 2: 28-35, 2005.*
Appendix showing sequence alignment.*

* cited by examiner

*Primary Examiner*—Jeffrey Stucker
*Assistant Examiner*—Aditi Dutt

(57) ABSTRACT

A novel cytosolic 58 kd phosphoprotein induced during bone marrow stem cell (BM) differentiation into dendritic cells (DC) during in vitro cultivation with the cytokine GM-CSF by addition of antisera to an 82 kd BM cell surface protein generating cultivatable dendritic progenitor cells (DP). Genes, methods for preparing them as well as early DP have been provided. Potential uses/advantages lie in the study of BM differentiation and innate immunity due to stimulatory/inhibitory DC, contribution of (BM) and DP to inflammation during infection and carcinogenesis, tumor promotion/regression, identification of BM-derived blood cells, T-cell activation/regulation/tolerance and inflammation.

8 Claims, No Drawings

SEQUENCE LISTING

<160> NUMBER OF SEQ ID NOS: 6

<210> SEQ ID NO 1
<211> LENGTH: 707
<212> TYPE: PRT
<213> ORGANISM: Mus musculus

<400> SEQUENCE: 1

```
Met Arg Leu Leu Ile Pro Ser Leu Ile Phe Leu Glu Ala Leu Gly Leu
 1               5                  10                  15

Cys Leu Ala Lys Ala Thr Thr Val Arg Trp Cys Ala Val Ser Asn Ser
             20                  25                  30
```

```
Glu Glu Glu Lys Cys Leu Arg Trp Gln Asn Glu Met Arg Lys Val Gly
            35                  40                  45

Gly Pro Pro Leu Ser Cys Val Lys Lys Ser Ser Thr Arg Gln Cys Ile
    50                  55                  60

Gln Ala Ile Val Thr Asn Arg Ala Asp Ala Met Thr Leu Asp Gly Gly
65                  70                  75                  80

Thr Met Phe Asp Ala Gly Lys Pro Pro Tyr Lys Leu Arg Pro Val Ala
                85                  90                  95

Ala Glu Val Tyr Gly Thr Lys Glu Gln Pro Arg Thr His Tyr Tyr Ala
                100                 105                 110

Val Ala Val Val Lys Asn Ser Ser Asn Phe His Leu Asn Gln Leu Gln
            115                 120                 125

Gly Leu Arg Ser Cys His Thr Gly Ile Gly Arg Ser Ala Gly Trp Lys
        130                 135                 140

Ile Pro Ile Gly Thr Leu Arg Pro Tyr Leu Asn Trp Asn Gly Pro Pro
145                 150                 155                 160

Ala Ser Leu Glu Glu Ala Val Ser Lys Phe Phe Ser Lys Ser Cys Val
                165                 170                 175

Pro Gly Ala Gln Lys Asp Arg Phe Pro Asn Leu Cys Ser Ser Cys Ala
                180                 185                 190

Gly Thr Gly Ala Asn Lys Cys Ala Ser Ser Pro Glu Glu Pro Tyr Ser
            195                 200                 205

Gly Tyr Ala Gly Ala Leu Arg Cys Leu Arg Asp Asn Ala Gly Asp Val
        210                 215                 220

Ala Phe Thr Arg Gly Ser Thr Val Phe Glu Glu Leu Pro Asn Lys Ala
225                 230                 235                 240

Glu Arg Asp Gln Tyr Lys Leu Leu Cys Pro Asp Asn Thr Trp Lys Pro
                245                 250                 255

Val Thr Glu Tyr Lys Glu Cys His Leu Ala Gln Val Pro Ser His Ala
            260                 265                 270

Val Val Ser Arg Ser Thr Asn Asp Lys Glu Glu Ala Ile Trp Glu Leu
        275                 280                 285

Leu Arg Gln Ser Gln Glu Lys Phe Gly Lys Lys Gln Ala Ser Gly Phe
    290                 295                 300

Gln Leu Phe Ala Ser Pro Ser Gly Gln Lys Asp Leu Leu Phe Lys Glu
305                 310                 315                 320

Ser Ala Ile Gly Phe Val Arg Val Pro Gln Lys Val Asp Val Gly Leu
                325                 330                 335

Tyr Leu Thr Phe Ser Tyr Thr Thr Ser Ile Gln Asn Leu Asn Lys Lys
                340                 345                 350

Gln Gln Asp Val Ile Ala Ser Lys Ala Arg Val Thr Trp Cys Ala Val
            355                 360                 365

Gly Ser Glu Glu Lys Arg Lys Cys Asp Gln Trp Asn Arg Asp Ser Arg
        370                 375                 380

Gly Arg Val Thr Cys Ile Ser Phe Pro Thr Thr Glu Asp Cys Ile Val
385                 390                 395                 400

Ala Ile Met Lys Gly Asp Ala Asp Ala Met Ser Leu Asp Gly Gly Tyr
                405                 410                 415

Ile Tyr Thr Ala Gly Lys Cys Gly Leu Val Pro Val Leu Ala Glu Asn
                420                 425                 430

Gln Lys Ser Ser Lys Ser Asn Gly Leu Asp Cys Val Asn Arg Pro Val
            435                 440                 445

Glu Gly Tyr Leu Ala Val Ala Ala Val Arg Arg Glu Asp Ala Gly Phe
```

```
                450             455             460
Thr Trp Ser Ser Leu Arg Gly Lys Lys Ser Cys His Thr Ala Val Asp
465                 470                 475                 480

Arg Thr Ala Gly Trp Asn Ile Pro Met Gly Leu Leu Ala Asn Gln Thr
                485                 490                 495

Arg Ser Cys Lys Phe Asn Glu Phe Ser Gln Ser Cys Ala Pro Gly
                500                 505                 510

Ala Asp Pro Lys Ser Asn Leu Cys Ala Leu Cys Ile Gly Asp Glu Lys
                515                 520                 525

Gly Glu Asn Lys Cys Ala Pro Asn Ser Lys Glu Arg Tyr Gln Gly Tyr
530                 535                 540

Thr Gly Ala Leu Arg Cys Leu Ala Glu Lys Ala Gly Asn Val Ala Phe
545                 550                 555                 560

Leu Lys Asp Ser Thr Val Leu Gln Asn Thr Asp Gly Lys Asn Thr Glu
                565                 570                 575

Glu Trp Ala Arg Asn Leu Lys Leu Lys Asp Phe Glu Leu Leu Cys Leu
                580                 585                 590

Asp Asp Thr Arg Lys Pro Val Thr Glu Ala Lys Asn Cys His Leu Ala
                595                 600                 605

Ile Ala Pro Asn His Ala Val Val Ser Arg Thr Asp Lys Val Glu Val
                610                 615                 620

Leu Gln Gln Val Val Leu Asp Gln Gln Val Gln Phe Gly Arg Asn Gly
625                 630                 635                 640

Gln Arg Cys Pro Gly Glu Phe Cys Leu Phe Gln Ser Lys Thr Lys Asn
                645                 650                 655

Leu Leu Phe Asn Asp Asn Thr Glu Cys Leu Ala Lys Ile Pro Gly Lys
                660                 665                 670

Thr Thr Ser Glu Lys Tyr Leu Gly Lys Glu Tyr Val Ile Ala Thr Glu
                675                 680                 685

Arg Leu Lys Gln Cys Ser Ser Ser Pro Leu Leu Glu Ala Cys Ala Phe
                690                 695                 700

Leu Thr Gln
705

<210> SEQ ID NO 2
<211> LENGTH: 20
<212> TYPE: PRT
<213> ORGANISM: Mus musculus

<400> SEQUENCE: 2

Lys Met Val Lys Tyr Leu Leu Glu Asn Ser Ala Asp Pro Asn Ile Gln
1               5                   10                  15

Asp Lys Ser Gly
                20

<210> SEQ ID NO 3
<211> LENGTH: 508
<212> TYPE: PRT
<213> ORGANISM: Mus musculus

<400> SEQUENCE: 3

Met Asp Glu Gly Ser Glu Val Ser Thr Asp Gly Asn Ser Leu Ile Lys
1               5                   10                  15

Ala Val His Gln Ser Arg Leu Arg Leu Thr Arg Leu Leu Glu Gly
                20                  25                  30

Gly Ala Tyr Ile Asn Glu Ser Asn Asp Arg Gly Glu Thr Pro Leu Met
```

-continued

```
            35                  40                  45
Ile Ala Cys Lys Thr Lys His Val Asp Gln Gln Ser Val Gly Arg Ala
    50                  55                  60
Lys Met Val Lys Tyr Leu Leu Glu Asn Ser Ala Asp Pro Asn Ile Gln
65                  70                  75                  80
Asp Lys Ser Gly Lys Ser Ala Leu Met His Ala Cys Leu Glu Arg Ala
                85                  90                  95
Gly Pro Glu Val Val Ser Leu Leu Lys Ser Gly Ala Asp Leu Ser
            100                 105                 110
Leu Gln Asp His Ser Gly Tyr Ser Ala Leu Val Tyr Ala Ile Asn Ala
        115                 120                 125
Glu Asp Arg Asp Thr Leu Lys Val Leu Leu Ser Ala Cys Gln Ala Lys
    130                 135                 140
Gly Lys Glu Val Ile Ile Thr Thr Ala Lys Ser Pro Ser Gly Arg
145                 150                 155                 160
His Thr Thr Gln His His Leu Asn Met Pro Pro Ala Asp Met Asp Gly
                165                 170                 175
Ser His Pro Pro Ala Thr Pro Ser Glu Ile Asp Ile Lys Thr Ala Ser
            180                 185                 190
Leu Pro Leu Ser Tyr Ser Ser Glu Thr Asp Leu Thr Leu Phe Gly Phe
        195                 200                 205
Lys Asp Lys Glu Leu Cys Gly Gly Ser Asp Asn Thr Trp Asp Pro Asp
    210                 215                 220
Ser Pro Pro Arg Lys Pro Val Ile Ala Thr Asn Gly Pro Lys Leu Ser
225                 230                 235                 240
Gln Ala Pro Ala Trp Ile Lys Ser Thr Pro Ser Leu Lys His Gln Ala
                245                 250                 255
Arg Val Ala Ser Leu Gln Glu Glu Leu Gln Asp Ile Thr Pro Glu Glu
            260                 265                 270
Glu Ile Ala Tyr Lys Thr Asn Ala Leu Ala Leu Ser Lys Arg Phe Ile
        275                 280                 285
Thr Arg His Gln Ser Ile Asp Val Lys Asp Thr Ala His Leu Leu Arg
    290                 295                 300
Ala Phe Asp Gln Val Asn Ser Arg Lys Met Ser Tyr Asp Glu Ile Asn
305                 310                 315                 320
Tyr His Ser Leu Phe Pro Glu Gly Ser Gln Thr Ser Val Glu Ile Pro
                325                 330                 335
Thr Asp Arg Asp Pro Asp Ser Asn Gln Ile Phe Ala Ser Thr Leu Lys
            340                 345                 350
Ser Ile Val Gln Lys Arg Asn Ser Gly Ala Asn His Tyr Ser Ser Asp
        355                 360                 365
Ser Gln Leu Ala Glu Gly Val Thr Pro Pro Thr Val Glu Asp Gly Lys
    370                 375                 380
Ala Ala Lys Lys Lys Ile Phe Ala Pro Ser Pro Ser Leu Leu Ser Gly
385                 390                 395                 400
Ser Lys Glu Leu Val Glu Pro Ala Pro Gly Pro Leu Ser Arg Arg
                405                 410                 415
Asn His Ala Val Leu Glu Arg Arg Gly Ser Gly Ala Phe Pro Leu Asp
            420                 425                 430
His Ser Leu Ala Gln Ser Arg Pro Gly Phe Leu Pro Leu Asn Val
        435                 440                 445
Asn Pro His Pro Pro Ile Thr Asp Ile Gly Val Asn Asn Lys Ile Cys
    450                 455                 460
```

```
Gly Leu Leu Ser Cys Gly Gln Lys Ala Leu Met Pro Thr Ala Pro Ile
465                 470                 475                 480

Phe Pro Lys Glu Phe Lys Thr Lys Lys Met Leu Leu Arg Arg Gln Ser
                485                 490                 495

Leu Gln Thr Glu Gln Ile Lys Gln Leu Val Asn Phe
                500             505

<210> SEQ ID NO 4
<211> LENGTH: 20
<212> TYPE: PRT
<213> ORGANISM: Mus musculus

<400> SEQUENCE: 4

Lys Met Val Lys Tyr Leu Leu Glu Asn Ser Ala Asp Pro Asn Ile Gln
  1               5                  10                  15

Asp Lys Ser Gln
            20

<210> SEQ ID NO 5
<211> LENGTH: 24
<212> TYPE: DNA
<213> ORGANISM: Mus musculus

<400> SEQUENCE: 5
cgcgttggtt ttgtaggcta tttc                                            24

<210> SEQ ID NO 6
<211> LENGTH: 24
<212> TYPE: DNA
<213> ORGANISM: Mus musculus

<400> SEQUENCE: 6
attcttctga gacggacctg acac                                            24
```

ANTIBODIES TO PROTEIN MARKERS ASSOCIATED WITH BONE MARROW STEM CELL DIFFERENTIATION INTO EARLY PROGENITOR DENDRITIC CELLS

CROSS-REFERENCE TO RELATED APPLICATIONS

The present application claims the benefit of U.S. Provisional Application No. 60/629,110, filed 18 Nov. 2004, which is hereby incorporated herein by reference.

SEQUENCE LISTING

The files titled "Sequence ID No. 1," created 10 Nov. 2005 and comprising 4,633 bytes, "Sequence ID No. 2," created 10 Nov. 2005 and comprising 376 bytes, "Sequence ID No. 3," created 16 Nov. 2005 and comprising 3,202 bytes, "Sequence ID No. 4," created 18 Nov. 2005 and comprising 663 bytes, "Sequence ID No. 5," created 18 November and comprising 287 bytes, and "Sequence ID No. 6," created 18 Nov. 2005 and comprising 287 bytes, each of which is included on the accompanying compact disc titled "Sequence ID Nos. 1-6," are hereby incorporated herein by reference.

DESCRIPTION

This invention resides in the discovery of a novel marker during differentiation of bone marrow stem (BM) cells into progenitors, the early stage of dendritic cells (DCs). Such protein is prepared by incubating BM cells with anti-DC antibodies, e.g., antisera, and then by isolating the protein, i.e., by separating it from the majority of components of a BM cell lysate following incubation with the anti-DC antibodies. The latter contains antibody to a BM cell surface 82 kd protein (CSP82). Specific antisera to CSP82 kd can also induce the novel marker.

The specific marker discovered by the inventors in mouse BM cell lysates is DP58. DP58 is a cytosolic phosphoprotein having a molecular weight of approximately 58 KD (SDS-PAGE), that is induced by incubation of BM cells with anti-DC or anti-CSP82 antibodies. The primary protein sequence of DP58, as determined by peptide mass fingerprinting, is provided in FIG. 2, below. Computationally predicted cDNA sequence of DP58 is also cited as accession no. NP_780664 (NCBI data base).

Having a marker for activation of BM differentiation is important for several reasons including because it allows scientists to determine what events trigger differentiation of undifferentiated progenitor DCs. In the absence of such marker, it is not practically possible to determine when differentiation has begun and therefore it is difficult to determine what events, e.g., cytokine induction, receptors involved in the initiation of differentiation, role and fingerprint of infiltrating bone marrow derived dendritic progenitors during infection and/or tumor growth/regression.

Thus, in one aspect, this invention comprises an anti-DP58 antibody, which can be used to readily identify when differentiation of BM cells to DCs has begun. The anti-DP58 antibodies of the invention include polyclonal as well as monoclonal antibodies, anti-DP peptide antibodies, as well as antibody derivatives, e.g., single chain antibodies and fragments and hybrids of antibodies and single chain antibodies, and other polypeptides that comprise a region that binds to the same epitopes as one or more polyclonal antibodies in antisera.

In a related aspect, this invention comprises a method for generating undifferentiated progenitor DCs comprising incubating BM cells with anti-DC antibodies or specifically with anti-CSP82 antibodies. Presence of a growth factor, e.g., GM-CSF, facilitates the development. Such cells are herein referred to as BM4 cells because they are optimally, but not only, produced by incubation of BM cells with anti-DC antisera for 4 hours.

The invention further resides in the discovery of a BM cell surface protein, CSP82, an 82 kd glycoprotein which is activated by anti-DC sera to induce expression of DP58. This protein can also be isolated, i.e., removed from BM cells, by techniques known to persons of skill in the art. Antibodies to CSP82 can also induce DP58, and generate BM4 progenitor cells from BM stem cells. In immunofluorescent staining, CSP-82 reveals itself as a surface protein and detergent is needed to solubilize it for biochemical studies. The protein was isolated by SDS-PAGE from immunoprecipitate prepared from lysates by using anti-DC antibody and confirmed by western blot. The SDS-PAGE-derived protein band of 82 kd was sequenced by HPLC-mass spectrometry as for DP58. The primary sequence of CSP-82 is shown below as Sequence ID No. 1:

```
                                                        Sequence ID No. 1
  1  MRLLIPSLIF  LEALGLCLAK  ATTVRWCAVS  NSEEEKCLRW  QNEMRKVGGP

51  PLSCVKKSST  RQCIQAIVTN  RADAMTLDGG  TMFDAGKPPY  KLRPVAAEVY

101  GTKEQPRTHY  YAVAVVKNSS  NPHLNQLQGL  RSCHTGIGRS  AGWKIPIGTL

151  RPYLNWNGPP  ASLEEAVSKF  FSKSCVPGAQ  KDRFPNLCSS  CAGTGANKCA

201  SSPEEPYSGY  AGALRCLRDN  AGDVAFTRGS  TVFEELPNKA  ERDQYKLLCP

251  DNTWKPVTEY  KECHLAQVPS  HAVVSRSTND  KEEAIWELLR  QSQEKFGKKQ

301  ASGFQLFASP  SGQKDLLFKE  SAIGFVRVPQ  KVDVGLYLTF  SYTTSIQNLN

351  KKQQDVIASK  ARVTWCAVGS  EEKRKCDQWN  RDSRGRVTCI  SFPTTEDCIV

401  AIMKGDADAM  SLDGGYIYTA  GKCGLVPVLA  ENQKSSKSNG  LDCVNRPVEG

451  YLAVAAVRRE  DAGFTWSSLR  GKKSCHTAVD  RTAGWNIPMG  LLANQTRSCK

501  FNEFFSQSCA  PGADPKSNLC  ALCIGDEKGE  NKCAPNSKER  YQGYTGALRC
```

```
-continued
551   LAEKAGNVAF LKDSTVLQNT DGKNTEEWAR NLKLKDFELL CLDDTRKPVT

601   EAKNCHLAIA PNHAVVSRTD KVEVLQQVVL DQQVQFGRNG QRCPGEFCLF

651   QSKTKNLLFN DNTECLAKIP GKTTSEKYLG KEYVIATERL KQCSSSPLLE

701   ACAFLTQ
```

Another aspect of the invention is antibodies directed to CSP82 (or unique peptides corresponding to specific regions of CSP 82 sequence) including, as discussed above, derivatives of such antibodies that retain binding specificity for the CSP82 epitopes.

One aspect of the invention includes a peptide having the sequence shown below as Sequence ID No. 2:

```
                                        Sequence ID No. 2
            IPIGTLRPYLNWNGPPASLE
```

Another aspect of this invention is the full length DP58 protein having the sequence shown below as Sequence ID No. 3 (and isoforms thereof):

```
1     MDEGSEVSTDGNSLIKAVHQSRLRLTRLLLEGGAYINESNDRGETPLMIAC

51    KTKHVDQQSVGRAKMVKYLLENSADPNIQDKSGKSALMHACLERAGPEVVS

101   LLLKSGADLSLQDHSGYSALVYAINAEDRDTLKVLLSACQAKGKEVIIITT

151   AKSPSGRHTTQHHLNMPPADMDGSHPPATPSEIDIKTASLPLSYSSETDLT

201   LFGFKDKELCGGSDNTWDPDSPPRKPVIATNGPKLSQAPAWIKSTPSLKHQ

251   ARVASLQEELQDITPEEEIAYKTNALALSKRFITRHQSIDVKDTAHLLRAF

301   DQVNSRKMSYDEINYHSLFPEGSQTSVEIPTDRDPDSNQIFASTLKSIVQK

351   RNSGANHYSSDSQLAEGVTPPTVEDGKAAKKKIFAPSPSLLSGSKELVEPA

401   PPGPLSRRNHAVLERRGSGAFPLDHSLAQSRPGFLPPLNVNPHPPITDIGV

451   NNKICGLLSCGQKALMPTAPIFPKEFKTKKMLLRRQSLQTEQIKQLVNF
```

The other aspect of the invention includes a peptide having the sequence shown below as Sequence ID No. 4:

```
            KMVKYLLENS ADPNIQDKSG
```

Another related invention is induction of DP58 from human cord blood stem cells by similar use of anti-DC antibodies as described earlier.

It will also be apparent to the person of ordinary skill in the art to prepare nucleotide sequences that encode DP58 or CSP82. Such sequences can be derived from mRNA to prepare cDNA or directly from genomic DNA, by genetic engineering techniques, e.g., PCR, cloning, or by synthetic techniques, e.g., direct synthesis of computationally determined sequences. Antisense DNA or RNA can also be prepared to suppress expression of DP58.

U.S. Pat. No. 6,479,286 discloses that IL-3 cultured expanded populations of monocytes are suitable for in vitro differentiation into DCs and describes various applications of said discovery. U.S. patent applications 2003/0104569 and 2003/0194803 are also of interest. These three references are incorporated herein by reference as though fully set forth.

This invention is more fully illustrated in the Examples that follow. This description is intended to be illustrative and not limiting. While this invention is described with respect to murine-derived DP58, it will be appreciated that analogous proteins exist in other species and can be isolated and utilized in accordance with this invention. Additionally, while this disclosure describes certain illustrative embodiments of the invention, including the preferred embodiments thereof, and uses thereof, other embodiments and uses will be apparent to persons of ordinary skill in the art.

EXAMPLES

Example 1

DP58

This existence of a common multipotent progenitor DC (pDC) implies that the commitment to DC occurs early in response to a specific cytokine microenvironment. Cytokines, GM-CSF in particular, function as the primary growth factor promoting mouse BM differentiation into DC, whereas GM-CSF and IL4 are both required for human hematopoietic stem cell (HSC) [1]. This ability of GM-CSF to induce mouse BM differentiation in vitro led us to develop specific antibody reagents for identifying molecular markers associated with the early events in DC development. We describe a novel cytosolic 58 KD Phosphoprotein associated with early DC progenitors when there is no clear-cut evidence of any specific DC subtype. Since this protein is induced during BM differentiation into common uncommitted early pDC [2,3], we designated it as DP58 after DC progenitors. The sequence of DP58 matches with no known protein sequences in the NCBI database, but it has been positively identified with a RIKEN cDNA in the Gene Bank with a Z score of 2.43 using peptide mass fingerprinting. To our knowledge, this is the first report implicating a cytosolic Phosphoprotein as one molecular hallmark of early DC progenitors. Unphosphorylated DP58 isoform has also been identified in adult neuronal nuclei using anti-DC and anti-DP58 antibody reagents, PCR technology, flow cytometry, and by fluorescent, and confocal microscopy. It is expected that like BCL3, DP58 functions as an anti-apoptotic mechanism in mature neurons. Thus, phosphorylated and unphosphorylated DP58 can be used to monitor differentiation status in developing brains as well as in diseased states.

Materials and Methods

Mice. BALB/c mice from Harlan Sprague Dawley (Indianapolis, Ind.) were bred in the animal facility of Indiana State University. The University Animal and Use Committee (ACUC) approved all animal experiments.

Cells and antibodies. Phenotyping was done using fluorescent monoclonal antibodies to CD11b, CD11c, MHCII, CD117, B220, CD86, and CD80 (all from eBioscence, USA), DEC-205 (Serotec, UK). Anti-phosphotyrosine (Zymed, USA) was used for biochemical characterization. Other materials included goat anti-rabbit-Ig HRP, rabbit anti-mouse-Ig (ICN, USA), and. Western Blot reagents were purchased from Pierce, USA).

Dendritic cells generation [4]. Bone marrow cells were prepared by flushing off the femurs and tibiae of BALB/c mice. Cells were cultivated in Iscove's modified Dulbecco's medium (IMDM) supplemented with 10% FBS and 10 ng/ml of recombinant murine Granulocyte macrophage colony stimulating factor (GM-CSF), (eBioscience & Peprotech, USA) for 6 days at 37° C. degree in 5% CO2. Non-adherent cells were removed on day 2 and 4 of culture, and fresh IMDM plus GM-CSF were added. DCs generated were phenotyped by flow cytometry and on a regular basis by fluorescent microscopy.

DC6 lysates preparation for antisera development: An emulsion containing equal volume of complete Freund's adjuvant (CFA) and DCs ($1-3 \times 10^7$ cells/ml) in 0.02% SDS solution in PBS was used to immunize three rabbits intradermally. Every 10 days they were bled and boosted with DC lysates emulsified in incomplete Freund's adjuvant (IFA).

Preparation of specific rabbit antibody reagents by repeated adsorption, salt fractionation has also been identified and protein A chromatography. The sera obtained after multiple immunizations were adsorbed primarily on splenocytes, liver tissues, dendritic cells, and myeloma X63-Ag8.653 cells. Further adsorption was done, as needed, with fresh or formalin-fixed BM cells. This was followed by 50% saturated ammonium sulfate precipitation, dialysis and protein A chromatography. One specific antibody reagent thus prepared was initially used to identify novel protein DP58 in dendritic cell progenitors.

Generation of progenitor BM cells. $1 \times 10^7$ BM cells were incubated with adsorbed rabbit antisera for 4 hr on ice to generate BM4 cells, which were then treated with 1 ml of a lysis buffer 12 containing 0.5% NP40 and 0.5% MEGA9 plus 10 µl of protease inhibitor, and left on ice for 30 min before analysis by SDS-PAGE.

SDS-PAGE and western blot. Lysates prepared according to Elvin et. al. [5] were subjected to 12.5% SDS-PAGE [6], followed by western blotting on nitrocellulose. Primary antibody was rabbit antisera (adsorbed with BM-fresh) and secondary antibody was commercially available antibody Goat anti-rabbit-Ig HRP. Super Signal West Pico chemiluminescent substrate (Pierce, USA) was used to visualize proteins on films.

Immunoprecipitation. This was done as described [6,7] using protein A to isolate specific immune complex formed by mixing cell lysates with the adsorbed rabbit antibody reagent. The specific protein band obtained by SDS-PAGE band was isolated and sequenced by peptide mass fingerprinting at the Proteomics Core Laboratory of Dr. Wang Mu, Indiana University School of Medicine.

Rabbit antisera against DP58 peptide: This was done using a conjugate of keyhole limpet hemocyanin (KLH) with a peptide, KMVKYLLENSADPNIQDKSG, as the immunogen (100 µg/injection). This was administered intradermally as an emulsion of the conjugate initially with CFA and later with IFA, and the rabbits, were bled at 10 days' interval. Purification was carried out by salt fraction using 50% saturated ammonium sulfate followed by affinity chromatography on KLH-sepharose column. Unbound fraction was the source of anti-DP58 antibody.

Results

Fifty-Eight KiloDalton Protein Identified as DP58

To identify DP58, the freshly harvested BM cells were treated with the adsorbed rabbit anti-DC antisera reagent on ice for 4 hr. This reagent was protein A-purified after repeated adsorption on BM-derived immature DCs and mouse myeloma as described in Materials and Methods. BM cells obtained after 4 hr incubation with the reagent, termed BM4 cells, were exposed to a lysis buffer, and the lysates were subjected to SDS-PAGE, and western blotting. We used for western blot the same specific antisera reagent but adsorbed additionally on fixed BM cells. Controls were run using lysates of BM cells that were treated with normal rabbit serum, rabbit anti-IgG or anti-CD11c monoclonal antibodies. The results showed that a 58 Kd protein (DP58) was detectable only in BM4 cell lysates using rabbit antisera reagent at 1:200,000 dilution. In contrast, the lysates of the fixed or fresh BM cells (undifferentiated) exhibited no DP58 protein, even with a higher concentration of the antibody reagent. Since DP58 protein was discerned only in the lysates of BM4 cells, but not of fresh or fixed BM cells, this suggests that this protein was induced as a cytosolic protein.

Next we determined the time course for induction of DP58. The results indicated that the induction was detectable in BM cells within 30 minutes, although the protein band was most discernible after 4 hr in BM4 cells. Clearly, this adsorbed rabbit anti-DC reagent facilitates differentiation of BM cells, possibly through cross-linking of a cell surface protein. To explore this possibility and to remove any antibody directed to any putative cell surface protein, we further adsorbed the purified anti-DP58 reagent repeatedly on formalin-fixed freshly isolated BM cells, and then used it to expose fresh and live BM cells for 4 hr. Interestingly, this adsorption of anti-DC reagent with fixed BM cells totally prevented fresh BM from differentiating into BM4 cells, but it still was capable of detecting DP58 protein in the lysates of existing BM4 cells. This indicates the presence of a cell surface molecule on fresh BM cells, which is needed for cytosolic DP58 induction. This observation was corroborated using anti-DP58 peptide antibody as described later.

DP58 Protein is Induced During BM Differentiation into DCs

To determine whether the BM4 cells (generated following incubation with rabbit anti-DC antisera) could differentiate into DCs, we cultivated them in GM-CSF for 6 days. No other cytokine such as IL4 displayed the ability to generate mouse DCs, as was also shown by others [1], and BM4 cells did not differentiate into DCs in the absence of GM-CSF. Phenotypic analyses revealed that BM4 cells differentiated into DCs that closely resembled CD8α-DCs generated from fresh BM using only GM-CSF. However while neither DCs expressed DEC-205, the DCs generated from BM4 cells had a very low expression of B220 marker. Since it was difficult to categorize these cells into either lymphoid or myeloid lineages, we consider BM4 cells as undifferentiated pDCs.

Isolation and Sequencing of DP58 from BM-Derived Cell Lysates

To determine if DP58 was a novel protein induced during BM differentiation into DCs, we purified it by immunoprecipitation and isolated the protein band following SDS-PAGE. This was then subjected to controlled tryptic digestion and the sequence of the peptides generated was positively identified with a computationally predicted RIKEN cDNA (NCBI data base accession NP_780664).

Next we addressed whether this novel cytosolically induced differentiation-related protein is a glyco- or Phosphoprotein. While the periodic acid-schiff staining for glycoprotein proved negative, the western blotting using a commercial anti-phospho-tyrosine antibody reagent indicated that DP58 was a phosphoprotein induced during BM differentiation.

Furthermore, to identify pDCs and study DC differentiation, we developed an anti-DP58-peptide reagent using the sequence identified as Seq ID 2. We used this antibody reagent to detect the presence of DP58 in unstimulated and stimulated BM cells as well as in DCs. The results showed that DP58 was undetectable in DCs possibly because of low levels of pDCs cells expressing of DP58. It was also evident that anti-peptide antibody recognized DP58 only in differentiating BM cells such as BM4 cell) lysates, and it could not stimulate fresh BM cells to differentiate. This was expected in view of the results in FIG. 1B, leading us to conclude that DP58 is the cytosolic marker of early progenitor DCs, possibly involved in signal transduction.

Discussion

This study is the first on a novel protein DP58 that was identified using a polyclonal anti-DC antibody reagent. The reagent was specifically prepared from antisera raised against the lysates of immature DCs that were generated following 6-day cultivation of, mouse BM cells in GM-CSF5. Before use, DCs were carefully phenotyped using fluorescent anti-CD11c, anti-CD11b, anti-CD8α, anti-MHC-II, anti-CD80, anti-CD86, anti-CD117, anti-B220, and anti-DEC205 monoclonal antibodies.

We reasoned that this cultivation of BM cells in GM-CSF should yield not only DCs, but also some undifferentiated BM cells that are at intermediate stages of development. The cell lysates from such heterogeneous DC-enriched (over 95%) population would likely contain various immunogenic molecules in a pecking order of immunogenicity derived from all cell types. This explains why our polyclonal antisera recognize not only the antigenic components of mouse DCs but also others associated with the differentiating BM cells. Importantly, the specific reagent prepared from these antisera readily detects DP58 protein only in differentiating BM cells within 30 min, and these differentiating BM cells develop into DCs when they are exposed to GM-CSF. Moreover, this induction of DP58 happens long before DCs emerge from BM cells following 6-day cultivation in GM-CSF. It suggests that DP58 occurs primarily in pre-DC population, and is highly immunogenic since the contribution of pre-DC population would be minimal in the DC lysate immunogen used to raise the antisera.

Identification of DP58 with a RIKEN cDNA in the database certainly advances our ability to identify many hypothetical proteins. The complex process of bone marrow differentiation into specific cell lineages such as dendritic cells involves numerous molecular interactions. Specific cytokines such as GM-CSF is known to drive mouse BM-associated HSC to DC-specific development and give rise to committed progenitor stem cells. Since GM-CSF or our specific antibody reagent can both cause BM cells to differentiate via induction of DP58 phophoprotein, and since the antibody reagent in particular detects DP58 in cell lysates within 30 min of BM cultivation as mentioned earlier, this is suggestive of ongoing intracellular events. Furthermore, the fact that anti-DP58 peptide antibody generated based on the sequence of DP58 also detects this protein only in lysates of differentiating but not fresh undifferentiated BM cells or DCs lends further support to this contention. This also suggests that this protein is induced as a result of activation and that this activation is possibly coordinated through a phosphorylation event.

Furthermore, to our knowledge, there is no specific method to generate and propagate early progenitors. On the basis of phenotypic studies, the BM4 cells reported here certainly fit the description of some of the early DC progenitors [8,9]. Since these cells can be cultivated for a short period in the absence of GM-CSF, it provides us the ability to clone or enrich and functionally characterize these DC progenitors from these cells. Further investigation is in progress to elucidate the physiological role and significance of BM4 cells in the context of DP58 induction during BM differentiation.

Example 2

CSP82

In this Example, we report identification and partial characterization of this cell-surface molecule as the mouse lactoferrin precursor glycoprotein, named CSP82. We show that both DP58 induction and the generation of early DC progenitors are mediated via this cell-surface protein. In contrast to lactoferrin found in milk, colostrums, and other mucosal secretions; CSP82, a member of iron-transporting transferrin family, occurs on naïve BM stem cells, but not on mature descendants. To our knowledge, this is the first report that lactoferrin precursor serves as a BM cell surface protein in the induction of a cytosolic differentiation marker DP58 associated with the emergence of a CD11b++Gr1++++B220+ progenitor DCs.

Materials and Methods

Mice. See, Example 1.

Antibodies. Antibodies were prepared substantially as described in Example 1 and as further described below.

DC Generation. DCs were generated substantially as described in Example 1. Generation of DCs from BM-derived stem cells. We first isolated hematopoietic stem cells (HSCs) using a commercial kit (from Stem Cell Technology, Canada) according to the manufacturer's protocol. The isolated HSCs were directly incubated at 4° C. with specific anti-CSP82 antibody for 4 hr generating BM4-HSC. Lysates from the latter were subjected to SDS-PAGE and Western blot analysis to demonstrate induction of DP58 as reported in Example 1.

Specific antibody reagents. Rabbit anti-DC antibody and anti-DP58 antibody reagents were prepared substantially as described in Example 1. These reagents were used respectively to generate progenitor DCs and detect DP58 on western blots. The rabbit anti DC Reagent A (henceforward referred to as Reagent A) was obtained by repeated sequential adsorption of anti-DC antisera at 4° C. on cells from spleen, liver, BM-derived mature and immature DCs and myeloma X63-Ag 8.653 until it tested negative on western blots of normal tissue lysates. Rabbit anti-DC Reagent B (henceforward referred to as the Reagent B) was prepared by further adsorption of Reagent A with formalin-fixed BM cells. Reagent A is capable of generating progenitor DCs and inducing marker protein DP58, whereas, Reagent B detects DP58 in pDCs but cannot induce it. These reagents were further purified on Protein A-agarose affinity columns.

Generation of early DC progenitors. This was done substantially as described in Example 1.

Identification of CSP82 by repeated adsorption. The initial identification, and isolation of CSP82 was done using Reagent A. This was confirmed using specific anti-CSR82 antibody developed subsequently.

Rabbit antisera against CSP82 peptide. The CSP82-specific Peptide (IPIGTLRPYLNWNGPPASLE)-conjugated to keyhole limpet hemocyanin (KLH) was used as the immunogen (100 μg/intradermal injection). Initially the conjugate was emulsified in Complete Freund Adjuvant (CFA) and subsequently in Incomplete Freund Adjuvant (IFA). Rabbits were boosted with CSPR82-peptide KLH, bled every 10 days, and the antisera was tested and purified by salt fractionation and affinity chromatography as described in Example 1.

Detection of CSP82 and DP58. Initially, reagent A was used to detect and isolate BM cell surface protein CSP82, while reagent B was used only to detect cytosolic DP58 in progenitor DCs. Detection and monitoring CSP82 and DP58 were subsequently performed using respectively specific anti-CSP82 peptide and anti-DP58 antibodies.

SDS-PAGE and Western blot. This was done substantially as described in Example 1.

Immunoprecipitation. Protein A was used to isolate immune complexes resulting from reactions of adsorbed rabbit antibody with fresh bone marrow lysates as described in Example 1. The protein band obtained by SDS-PAGE was sequenced by peptide mass fingerprinting at proteomics Core Laboratory of Dr. Wang Mu, Indiana University School of Medicine, Indianapolis.

Results

The 82 kilodalton protein CSP82 identified on the cell surface of fresh murine BM cells To identify CSP82, freshly harvested BM cells of naïve BALB/c mice were subjected to SDS-PAGE and western blotting. The blot was analyzed using the purified rabbit antibody Reagent A. The results showed that the CSP82 protein band was detectable only in lysates of fresh BM cells, and this was possible only when non-ionic detergents like NP-40 were used. No such band was discernible in similar lysates from mature and immature DCs (IDCs), progenitor DCs (BM4), splenocytes, or myeloma cells. However, the CSP82 protein was undetectable in the lysates of BM and other cells if the antibody Reagent B was used for western blotting. Clearly, the adsorption of rabbit antibody Reagent A on fixed-BM cells removed the antibody necessary for detection of CSP82 present on fresh BM cells.

To assess whether CSP82 is associated with HSCs in freshly harvested BM cells, a commercial kit from Stem Cell Biotechnology was used to isolate and purify HSCs. Proteins in lysates of HSCs were then separated by SDS-PAGE and analyzed by western blot. Results revealed the presence of CSP82 in HSC lysates when the western blot was probed with Reagent A. However, with Reagent B the protein band corresponding to CSP82 was undetectable, although the same reagent could detect, as expected, DP58 in the same BM4 lysates. Thus the antibody Reagent A specifically recognized CSP82, an 82 kd protein in fresh BM cells.

We confirmed the above finding came from the immunofluoresence studies on fresh BM cells showing that CSP82 protein on these cells is recognized by Reagent A and anti-CSP82 antibody only.

Isolation and Sequencing of CSP82 from Fresh BM ysates

We isolated and purified the 82 kd protien band (CSP82) by immunoprecipitation from lysates and separation by SDS-PAGE. This protein was then subjected to tryptic digestion, and sequencing by peptide mass fingerprinting. The sequence of CSP82 was identical to that of the murine lactoferrin precursor protein [11,12].

Development of Rabbit CSP82 Peptide-Specific Antibody

To better characterize CSP82 and determine its role in DC generation, we developed a rabbit anti-CSP82 peptide antibody reagent using the peptide sequence of Seq ID 2. This peptide sequence is also identical to that in secreted lactoferrin [12]. We reasoned that antibody to this peptide would not only confirm the identity of CSP82 with the lactoferrin group of proteins, but also establish the existence of both membrane and secreted forms of lactoferrins. Furthermore, this antibody was used to confirm our earlier findings with the reagent A that CSP82 is present on naïve BM or stem cells. The results showed that anti-CSP82 peptide antibody could detect CSP82 as well as secreted lactoferrin in BM lysates of fresh but not fixed BM cells. It is interesting to note that the specific anti-CSP82 peptide antibody recognized also the cytosolic lactoferrins of about 52 kD in both BM4 and HSC-BM4. Furthermore, incubation of fresh BM cells with this specific reagent induced progenitor DC, i.e., BM4 cells and expression of the cytosolic protein, DP58. Furthermore, when fresh BM cells were incubated with anti-CSP82 reagent, they underwent transformation into BM4-like cells and induction of DP58, as was seen, by the use of Reagent A. The results clearly indicate that CSP82 was the BM cell surface protein recognized by antibody Reagent A and anti-CSP82. Moreover, binding of either antibody could induce development of BM cells into Pro-DC BM4 cells and induce expression of DP58 phosphoprotein. Interestingly, antibody Reagent A, unlike the anti-CSP82 peptide antibody, recognized only CSP82, or the membrane form of lactoferrin implying that the latter as a mature surface protein might have unique epitopes, due possibly to posttranslational modifications that facilitate its localization on cell surface.

CSP82 is a Glycoprotein

Glycoprotein staining and an antiphosphotyrosine antibody were used to determine whether CSP82 on BM cells is a glyco- or phosphoprotein. Proteins of detergent-solubilized BM cell lysates were separated using SDS-PAGE and then stained using a Pro-Emerald 300 glycoprotein stain kit (Molecular Probe, USA). The staining positively identified CSP82 as a glycoprotein. However, CSP82 protein proved to be unphoshphoprotein, unlike the cytosolic DP58, and this was shown by western blot analysis using a commercially obtained an anti-phosphotyrosine antibody.

Phenotypic Characterization of Different BM Cells

We used techniques of immunofluorescence to characterize fresh and differentiating BM cells, as mentioned earlier. Controls run with normal pre-bleed also proved negative. We also determined whether typical DC developmental markers were present on BM4-like cells. Such cell surface markers as CD11b, Gr 1, B220 were easily discernible using commercial monoclonal antibodies as the BM cells differentiated into pro-DC BM4 cells.

Discussion

To our knowledge, this is the first example that shows a novel mouse lactoferrin precursor protein (CSP82) is present on undifferentiated BM cells or HSCs (hematopoietic stem cells), but not on their descendants. Similar to many membrane proteins, CSP82 appears to be a glycoprotein. It is interesting to note that the membrane form of 82 kD lactoferrin described here is identical in amino acid sequence to the secreted lactoferrin which can be of various molecular sizes up to 79 kD. The difference in the nominal molecular sizes between CSP82 and secreted lactoferrin may lie in the hydrophobic sequences that are necessary to be a membrane-associated protein. BM-associated mouse CSP82 has considerable sequence homology with a human melanoma protein, melanotransferrin p97, which is a membrane form of serum Fe-binding protein transferrin and human lactoferrin. [11]. We believe that CSP82, like this membrane-bound p97, has a glycosyl-phosphotidylinositol (GPI) moiety as the membrane anchor. This is a posttranslational lipid modification that occurs in endoplasmic reticulum. Experiments are in progress to address this issue.

Occurrence of a lactoferrin member on BM stem cells must be of immense biological significance. Lactoferrin, an iron-binding glycoprotein in milk and other exocrine secretions, is known to have multiple functions, notably anti-microbial properties and the ability to modulate the immune system by release of anti-inflammatory cytokines from monocytes and by regulation of cellular proliferation and differentiation [12-14]. The anti-microbial property of lactoferrin from leukocytes is due to its ability to bind and inactivate LPS [24]. Our finding of a lactoferrin precursor protein on BM or HSC suggests that it may serve as a receptor for LPS-like ligands promoting differentiation of BM cells along CD11b+/Gr 1+ myeloid lineages. There are reports on the presence of estrogen and growth factor response modules in the mouse lactoferrin gene [12,13]. This suggests that the expression of lactoferrin protein as a cell surface receptor on stem cells may be responsive to environmental estrogenic substances, which in turn may influence on BM differentiation and proliferation [13].

This example also shows that crosslinking of this cell surface protein on BM cells by antibody Reagent A or by the anti-CSP82 antibody sets in motion a differentiation event in which BM stem cells become committed to the DC progenitor pathway.

Finally, the physiological role of CSP82 in HSC remains speculative. The interaction of CSP82 with microbial LPS may serve two purposes: (1) protect HSCs from microbial infections, and (2) trigger a novel cytosolic phosphoprotein DP58-mediated differentiation pathway leading to DCs. The latter as APCS can up or down regulate acquired immunity involving B and T cells. Lactoferrin is an iron-binding protein, so it is possible that iron is a natural ligand for CSP82. Iron availability has been shown to influence expression of the cyclin-dependent kinase inhibitor P21 during differentiation of DCs from human peripheral monocyte precursors [15].

Example 3

DP58 Expression in Brain Cells

As a first step to understand the physiological roles of DP58 in the context of BM differentiation, we evaluated the tissue-specificity of DP58 and its phospohorylation status. Using biochemical and molecular techniques we show that DP58 is constitutively expressed in brain but primarily as an unphosphorylated protein. Moreover, immunocytochemical studies demonstrate the presence of DP58 in neurons of the basal ganglia, brainstem and neocortex of adult mice brains. It appears that DP58 is primarily localized in the cell nuclei of cultured neurons. Because its expression is tissue-specific, DP58 as a nuclear protein marker may prove useful to monitor HSC differentiation into neuronal cells. To our knowledge, this is the first report of a common protein shared between mature neuronal cells and differentiating bone marrow-derived progenitor cells.

Materials and Methods

Mice—See, Example 1.

Antibody reagents—For phenotypic characterization of immature DCs and BM progenitors, we used following monoclonal antibodies conjugated to FITC, and directed to MHC class 11, CD11b, B220, CD86, CD11c, CD8α, CD80 and CD117 (all from eBioscience, USA). Antibodies to phosphotyrosine, phosphoserine and phosphotheronine were obtained from Zymed, USA. These were used in western blotting to determine the phosphorylation status of DP58 in Pro-DCs and brain cells. Some reagents for western blotting and immunocytochemistry were purchased from Pierce (USA). Others were obtained as listed: anti-rabbit-HRP (ICN, USA) goat anti-rabbit Cy3, goat anti-mouse Cy2, (Amersham, USA).

DC generation—DC cells were prepared substantially as described in Example 1.

Raising antibodies against immature DC lysates—Anti-DC polyclonal antibodies and anti-DP58 antibodies were generated substantially as described in Example 1.

DP58 protein—DP58 was isolated from BM cells substantially as described in Example 1.

SDS-PAGE and Western blot—All lysates were prepared and subjected to SDS-PAGE substantially as described in Example 1. Proteins were then transferred onto nitrocellulose for western blotting. The latter was developed with rabbit anti-DP58 peptide as the primary antibody, followed by goat anti-rabbit-Ig-HRP, and Super Signal West Pico chemilumininescent substrate to visualize labeled proteins on film.

The range of DP58 occurrence in different tissues—The presence of DP58 in various tissues was examined by screening multiple tissue-specific cDNAs (MTC Panels cat no. #K1441-1 and #K1430-1 from BD Biosciences clontech, USA) by PCR. The MTC panels included cDNAs from mouse heart, spleen, and lung, liver, skeletal muscle, kidney, testis, embryos of various ages, bone marrow, eye, lymph node, smooth muscle, prostate, thymus, uterus, and stomach. We also screened for DP58 by PCR, freshly isolated bone marrow cells, brain tissues, progenitor DCs (BM4 cells), immature and mature DCs from mice of various ages and confirmed by sequencing of the amplified DNA band.

Reverse-transcriptase mediated polymerase-chain reaction (RT-PCR)-. Analysis of the expression of DP58 was carried out using RT-PCR essentially as described [16]. The forward primer used was 5'-ATTCTTCTGAGACGGACCT-GACAC-3' and the reverse primer consisted of 5'-CGCGT-TGGTTTTGTAGGCTATTTC-3'. Total RNA samples were extracted using the RNAqueous system (Ambion, USA). Reverse transcription reactions were carried out using 1 μg of total RNA purified from indicated sources. Each reaction consisted of 60 μl of which 25 μl was the RNA and water. The RNA was denatured for 3 min. at 70° C. then chilled on ice and the remaining reagents were added such that the reaction contained 1× reverse transcriptase buffer, 1 mM MgCl2, 0.5 mM all 4 dNTPs, 0.5 - 1 μl RNase inhibitor (Promega, USA.), and 100 pmole of random hexamers. The primers were allowed to anneal to the RNA at room temp for 5-10 min. Lastly, 200 U SuperscriptRT (Invitrogen, Inc.) was added and the reactions incubated for 60 min at 37° C. The RNA template was degraded by incubation with 1 μg of RNaseA at 37° C. for 15 min.

For end-point PCR reactions, an amount of the RT reaction equivalent to 16.7 ng of input RNA was subjected to the PCR. The reaction volume was 25 μl containing, 1× PCR buffer, 250 μM all 4 dNTPs, 2 mM MgCl2, 10 pmole of each specific PCR primer, and 2-3 units Taq polymerase. Reactions were standard 30 cycle PCRs with conditions involving an initial 5 min. 95 C denaturation followed by 3040 cycles of 95° C. for 30 sec, 62° C. for 30 sec, 72° C. for 30 sec. Following PCR, 10-15 μl of each reaction was analyzed by agarose gel electrophoresis and photographed by UV transillumination. As a control for RNA loading into the RT reaction, expression of *Mus musculus* glyceraldehyde 3-phosphate dehydrogenase (G3PDH) was analyzed using a 25-cycle PCR. When expression was to be quantified by quantitative PCR (see below), the 60 μl RT reaction was first diluted to 6-fold and 1 μl of the diluted RT was used as template for each qPCR.

Quantitative PCR (qPCR)- Quantitative PCR was performed utilizing the Mx3000P PCR machine (Stratagene, USA.). Fluorescence detection chemistry involved utilization of SYBR green dye master mix (Bio Rad, USA.) and HPLC purified qPCR primers at 150 nM. Each qPCR utilized 2.5 ng equivalents of input RNA from each RT reaction. All qPCR reactions were carried out in triplicate and used a 40-cycle program whose time and temperature parameters were the same as for end-point PCR. Melting-curve analysis of all products demonstrated a single peak, indicating that each set of primers produced a single product. Each RT reaction was equalized for RNA input by assessing the level of expression of the relatively invariant housekeeping gene, G3PDH. To determine quantitative values, standard curves were generated with each primer pair using a 5× dilution series ranging from 16.7 ng to 0.27 ng RNA equivalents of an RT. Expression of DP58 was then equated to the normalized input of G3PDH.

Immunohistology and immunohistochemistry-Adult mice were euthanized with an overdose of sodium pentobarbital and transcardially perfused with neutral-buffered 4% paraformaldehyde. The brains were removed and post-fixed in the same fixative for 1 hour at room temperature on the shaker. They were then cryoprotected by immersion overnight in Tris-buffer (pH 7.4) with 30% sucrose. The brains were sectioned on a cryostat at a thickness of 40 μm. The sections were processed free-floating for immunohistochemistry as follows. All rinse steps were performed using Tris-buffer (pH 7.4). Sections were first incubated in methanolic peroxide for 15 minutes to remove endogenous peroxidase and, following a rinse step, blocked with 5% non-fat dry milk for one hour at room temperature. They were then directly transferred to the primary antibody, DP58, diluted 1:500 in 5% non-fat dry milk for 2 hours at room temperature and then overnight at 4 oC. The next day, following a rinse step, the sections were incubated in peroxidase-conjugated goat anti-rabbit secondary antibody (diluted 1:100) for 3 hours at room temperature on the shaker. Following another rinse step, the immunolabeling was visualized by incubation with diaminobenzidine and hydrogen peroxide. The sections were mounted on alcohol-gelatinized slides and cover-slipped with Permount.

A similar procedure was used for immunohistofluorescence with the following differences: no endogenous peroxidase step was performed; the blocker was 3% normal goat serum; the primary antibody was mixed in 1% normal goat serum; and the secondary antibody was Cy3-linked goat anti-rabbit IgG, diluted 1:1000.

Sections were also double-labeled using DP58 antibody and a mouse antibody to microtubule-associated protein 2 (MAP2; Sigma product # M-1406; diluted 1:250) as a neuronal marker. The secondary antibodies were Cy3-linked goat anti-rabbit IgG and Cy2-linked goat anti-mouse IgG, both diluted to 1:1000.

Primary neuron culture: The primary neuron culture method was adapted from Brewer [17]. Briefly, the hippocampus was isolated by dissection from mice brain, minced on a tissue chopper, incubated in Hibernate A (Gibco), and then treated with Papain (Worthington). The tissue was then triturated 10 times and the supernatant collected. The sediment was resuspended in Hibernate A/B27 (Gibco) and triturated again. This procedure was repeated once more with the supernatant saved each time. The collected supernatant was then layered on an Opti-Prep gradient and centrifuged for 15 minutes at 1900 rpm. The volume above the white suspension layer containing the neurons was discarded and the white suspension layer was transferred into Hibernate A. This was centrifuged at 1100 rpm at room temperature. The supernatant was discarded and the pellet resuspended in B27/Neurobasal A (Gibco). The neurons were plated at a density of $1 \times 10^7$ in Poly-D-Lysine-coated glass 96-well culture plates containing B27/Neurobasal A. The cells were incubated for 1 hour at 37 oC in 5% CO2, rinsed with fresh B27/Neurobasal A at 37 oC then Hibernate A and incubated in growth medium. The cells were fed every other day and allowed to grow for 1 week before experiments were conducted.

Results

DP58 Expression in Different Tissues

Expression of DP58 protein in various tissues was assessed by screening PCR multiple tissue-specific cDNAs (MTC Panels) using DP58-specific primers. The results indicated that only the cDNA from brain tissues could be amplified using DP58-specific primers. Further corroboration of this finding came from RT-PCR and qPCR analyses of DP58 expression in freshly isolated whole brain, bone marrow cells, and cells generated during DC differentiation. DP58 expression at the mRNA level in unstimulated brain far exceeded the levels seen in BM cells even after 40 cycles of PCR. The expression of DP58 message in brain and bone marrow was quantified by qPCR. Brain tissue expressed approximately 1200 times more DP58 mRNA than BM cells, particularly in dendritic progenitor cells BM4, when all DP58 levels were normalized with respect to the housekeeping gene G3PDH. Interestingly, DP58 mRNA level was four times higher in cycloheximide treated BM4 cells than in untreated BM4 cells indicating that the factor(s) required for DP58 transcription are already present prior to the induction of BM cells [18]. Treatment with cycloheximide was indeed inhibitory upon protein synthesis as reflected by the fact that the level of DP58 protein was not increased fourfold in concert with that of the mRNA. Our result also indicated that unlike DCs, brain tissues constitutively expressed DP58 protein.

DP58 Protein Expression in Brain and Bone Marrow Cells

The demonstration that levels of DP58 mRNA level were higher in brain than in bone marrow cells raised the question of whether similar relative concentrations would be observed at the protein level in both tissues. By SDS-PAGE and Western blotting, we showed that contrary to what was seen with RT-PCR, DP58 protein is much higher in BM4 cells than in brain. Also, the estimated molecular weights were different. In brain tissue, DP58 migrated with an apparent MW of 52 KDa. Even though only BM4 cells express DP58 protein, both BM4 and immature DCs expressed similar levels of DP58 mRNA. Furthermore, in spite of several-fold high DP58 mRNA expression in unstimulated whole mouse brain tissue, it did not translate into proportionally high DP58 protein levels.

Comparison of DP58 Nucleotide Sequences from Brain and BM 4 Cells

The PCR products derived from brain and bone marrow, using the DP58-specific primers were sequenced and shown to be identical. In addition, the sequences were identical to the corresponding region of the RIKEN cDNA identified as DP58.

Demonstration of DP58 Expression in Brain by Immunohistology

Using the DP58 peptide-specific antibody (Reagent A)—we performed immunohistology on brain tissue sections. The results showed DP58 immunoreactivity in all mouse brain regions. The nuclei of nerve cells were immunolabeled in all cortical layers, in the pyramidal layer and the dentate granular layer of the hippocampal formation, in the basal ganglia and brainstem. A closer look revealed that the nuclear labeling consisted of a diffuse labeling of the entire nucleus and an intense labeling of bodies, approximately 5 μm in diameter. In the neocortex, the intense labeling appeared primarily at the periphery of the 5 μm bodies. In the brainstem, the labeled bodies were more punctate in appearance and could also be seen in the perikaryon. The same pattern of immunoreactivity was also seen in the cerebellum, where the nuclei of Purkinje cells were clearly labeled, although the nuclei of granule cells were not. These results confirm that DP58 is a cytosolic protein in BM4 and suggest that DP58 may be synthesized in the neuronal perikaryon and subsequently transported into the nucleus.

DP58 protein was localized in stimulated BM cells (BM4) and in nerve cells using confocal microscopy in conjunction with specific antibody regents (rabbit anti-DCs) and goat anti-rabbit Cy3. As a control, normal goat serum was used instead of the primary antibody. The results showed DP58 localized to the nuclei of nerve cells but in BM4 cells, DP58 labeling was cytoplasmic. Cells labeled by the DP58 antibody were also labeled by the MAP2 antibody, an antibody that is specific for neurons. As shown in previous study by Western blotting [19], DP58 was detectable only as a cytosolic protein in BM4 Pro-DC cells. The method control was run with normal goat serum.

Post-Translational Modification of DP58 in Different Tissues

Since SDS-PAGE and western blotting of DP58 from BM4 cells and brain revealed two distinct molecular species, 58 KDa and 52 KDa respectively, it was of interest to determine if post-translational modification would account for the difference. We performed SDS-PAGE and western blotting of brain tissue, naive BM and BM4 cells using commercially obtained anti-phosphotyrosine, antibodies. The results indicated specific phosphoprotein nature of DP58 in BM4 cells only but not in brain. Thus, DP58 occurred as an unphosphorylated 52 kDa nuclear protein in brain while in pro-DC cells, DP58 is Phosphorylated [19].

Discussion

The evidence presented in this example clearly shows that DP58 expression does not occur exclusively in BM-derived early progenitor DCs. Expression of this novel molecule is also observed in brain tissues. Using qPCR we have demonstrated that there is 1200 times more of DP58-specific mRNA in mouse brain than in BM-derived BM4 cells. However, BM4 cells express higher levels of DP58 protein than do brain tissues. Parallel sequencing of the products of PCR-amplified DP58 from brain tissue and BM4 cells reveals complete identity with the DP58 protein sequence.

The two interesting points emerge from analyses of the results of this study. First, of all tissues, only cells of the immune system and brain express DP58, and these tissues are derived from different germ layers. Immunocytochemical studies clearly indicate that DP58 is predominantly located in neuronal nuclei, whereas in BM4 cells, it is cytosolic. The two proteins also differ in observed molecular weight; the 58 kDa a protein in BM4 cells is a phosphoprotein, while in neuronal cells it is a 52 kDa unphosphorylated protein. The apparent difference in size may be due to phosphate moieties in DP58. The other noteworthy point is that although at the mRNA level, the brain tissues exhibit considerably higher levels of DP58 than in BM4 cells, this does not happen proportionately at the protein level. Western blot analysis using the same protein amounts from brain and BM4 cells shows that the expression is highest in the latter. In BM-derived progenitors, the protein is induced during BM4 differentiation, whereas in nerve cells from diverse regions such as cortex, brain stem, and basal ganglia, DP58 expression occurs constitutively. A low detectable level of immunostainable cytosolic DP58 is, however, also discernible in nerve cells by immunocytochemistry. It remains to be determined whether the cytoplasmic neuronal protein is phosphorylated as in BM4 cells.

An issue of interest is why brain cells express significantly higher levels of DP58 mRNA, and yet at the protein level, expression is even less than that in BM4 cells. Also intriguing is the fact that the level of DP58 mRNA is higher in naïve BM cells than in BM4 cells, yet the protein is higher in the converse order. To address this disconnect between the levels of DP58 mRNA and protein, we treated cells with cycloheximide to inhibit protein synthesis. It is apparent from our study that cycloheximide causes DP58 mRNA levels to rise four fold in BM4 cells, but when the same cells were analyzed at the protein level, they did not register proportionately higher values. Thus, it appears irrespective of whether it is in brain or BM4 cells that the translation of specific mRNA into DP58 protein is highly regulated. Since the transcription process does not seem to be hindered, this regulation possibly occurs at the post-nuclear processing stages. However, it may be likely that the BM4 induction process leads to the activation of a regulatory pathway resulting in DP58 mRNA degradation. The synthesis of the enzyme responsible for this mRNA turnover is likely to be inhibited in the presence of cycloheximide thus accounting for the 4-fold increase in DP58 mRNA in inhibitor treated cells.

The differences in DP58 occurrence between brain and BM4 cells may be explained in terms of their differentiation status. BM4 cells represent differentiating DC progenitors, whereas neurons are adult quiescent cells unlikely to respond to any differentiation stimuli. Nuclear location of DP58 in neurons may reflect an anti-apoptotic property to maintain $G_0$ status in a manner similar to that observed with BCL3 proteins [20]. Neurogenesis and neuronal maturation may accompany redeployment in the nuclei of DP58 as an unphosphorylated constitutive protein from an inducible cytosolic phosphoprotein.

During neurogenesis, i.e., in a child over 2 years of age, when neurons reach some stages of maturity, DP58, as an important anti-apoptotic facor is expected to be expressed and deployed in neuronal nuclei as an Indication of a normal developmental process. Any changes in the level of DP58 may be a phenotypic measure of neuronal viability or general developmental problem. In pre-natal stage too, it may have implications in health of developing fetuses. In cases of neuroblastoma, DP58 expression may significantly vary due to persistence of immature neurons. Any treatment modality that improves the condition may benefit by monitoring DP58 level in effluent cells or biopsies. ELISA, RIA or PCR will reveal these changes. In diseases like Alzheimer's Disease or others, the measurable levels of DP58 would be indicative of infiltration of cells like dendritic cells and the consequent immunological reaction or neuronal degeneration and dysfunction.

REFERENCES

1. J. I. Mayordomo, Zorina, T., Storkus W. J. et al. Bone marrow-derived Dendritic cells serve as adjuvants for Peptide-based antitumor vaccines. Stem cells 15 (1997) 94-103.
2. G. M. del Hoyo, P. Martin, H. H. Vargas, S. Ruiz, C. F. Arias, C. Ardavin, Characterization of a common precursor population for dendritic cells. Nature 415 (2002) 1043-1047.
3. A. D. Amico, L., Wu. The early progenitors of mouse dendritic cells plasmacytoid predendritic cells are within the bone marrow hematopoietic precursors expressing Flt-3. J. Exp. Med.198 (2003) 293-303.
4. L. Krishnan, S. Sad, G. B. Patel, G. D. Sportt, The potent adjuvant activity of arschaeosomes correlates to the Recruitment and activation of macrophages and dendritic cells in vitro. Journal of immunology 166 (2001) 1885-1893.
5. J. Elvin, C. Potter, T. Elliott, V. Cerundolo, A. Townsend, A method to quantify binding of unlabeled peptides to class I MHC molecules and detect their allele specificity, J. Immunol. Methods 158 (1993) 161-171.
6. S. K. Ghosh, P. Patnaik, R. B. Bankert, Expression of μ and γ membrane forms of immunoglobulin segregate in somatic cell hybrids. Mol. Immunol. 24 (1987) 1335-1343.
7. S. Gallagher, S. E. Winston, A. Steven, J. G. R. Hurrell, Isolation and analysis of proteins. Current protocol in immunology 4 (2000) 1-3.
8. M. G., Manz, D. Traver, T. Miyamoto, I. L. Weissman, K. Akashi, Dendritic cell potentials of early myloid and lymphoid progenitors. Blood 97 (2001) 3333-3341.
9. C. Ardavin, Origin, precursors and differentiation of mouse dendritc cells. Nature Rev. Immunobiol. 3 (2003) 582-591.
10. M. F. Lipscomb, B. J. Masten, Dendritic cells: immune regulators in health and disease. Physiol. Rev. 82 (2002) 97-130.
11. R. G. Woodbury, J. P. Brown, M.-Y. Yeh, K. E. Hellstroem, I. Hellstroem, Identification of a cellsurface protein, p97, in human melanoma and certain other neoplasms, Proc. Natl. Acad. SCi. USA 77 (1980) 2183-2187.
12. B. T. Pentecost & C. T. Teng, Lactotransferrin is major estrogen inducible protein of mouse uterine secretions, J Biol. chem, 262 (1987) 1034-1039.
13. C. T. Teng, Mouse lactoferringen: a marker for estrogen and EGF. Enviro Heaith. Prespect. 103 (1995) 17-20.
14. O. M Conneely, Anti-inflammatory activities of lactoferrin. J Amer. Coll. Nutri. 20 (2001) 389S-395S.
15. J. L. Kramer, I. Baltathakis, O. S. F. Alcantara, D. H. Boldt, Differentiation of functional Dendritic cells and macrophages from human peripheral blood monocyte precursors is dependent on expression of p21 (WAF1/CIP1), Brit. J. Hematol. 117 (2002) 727-734.
16. King, M. W., Ndiema, M. and Neff, A. 1998. Anterior structural defects by misexpression of Xgbx-2 in early *Xenopus* embryos are associated with altered expression of cell adhesion molecules. Dev. Dyn. 212, 563-579.
17. Brewer, G. J. 1997.) Isolation and culture of adult rat hippocampal neurons. J. Neurosci. Meth. J. Neurosci. Meth. 71, 143-155.
18. Mohn, K L, Laz T. M., Hsu, J C, Melby, A. E, Bravo, R., Taub, R. 1991. The immediate-early Growth response in regenerating liver and insulin-stimulated H-35 cells: comparison with serum-stimulated 3T3 cells and identification of 41 novel immediate-early genes. Mol Cell Biol. 11(1), 381-390.
19. Jiang, Y., Naessen, B., Lenvik, T., Blackstad, M., Reyes, M., Verfaillie, C. M. 2002. A new Antigen common to the rat nervous and immune systems: I. Detection with a hybridoma. Experimental Hematol. 30, 896-904.
20. Bundy, D. L., and Mckeithan, T. W. 1997. Diverse effects of BCL3 phosphorylation on its modulation of NF-kappaB p52 homodimer binding to DNA. J Biol Chem, 272, 33132-33139.

The invention claimed is:

1. An isolated antibody that
   (a) binds to the cytosolic phosphoprotein that
      (i) is induced during differentiation of BM cells to dendritic cells and
      (ii) is induced in bone marrow (BM) cells by incubation of the cells with antisera raised against a dendritic cell lysate following adsorption of the antisera with splenocytes, liver cells, dendritic cells, and myeloma cells, wherein the dendritic cells used to prepare the lysate are DC-enriched (over 95%) and also comprise BM cells at intermediate stages of differentiation and
      (iii) is not induced by said antisera following further absorption of the antisera with fresh or formalin-fixed BM cells and
   (b) binds to the peptide of SEQ ID NO: 4.

2. The isolated antibody of claim 1 prepared by immunization with SEQ ID NO: 4.

3. The isolated antibody of claim 2 wherein the peptide of SEQ ID NO: 4 is conjugated to keyhole limpet hemocyanin.

4. The isolated antibody of claim 3 prepared by intradermally administering an emulsion of the conjugate with an adjuvant.

5. The isolated antibody of claim 1 wherein the cytosolic phosphoprotein is also induced by incubation of BM cells with anti-CSP82 antisera.

6. The isolated antibody of claim 1 wherein the cytosolic phosphoprotein is induced within 30 minutes of incubation of the cells with the antisera.

7. The isolated antibody of claim 1 wherein the cytosolic phosphoprotein is present in brain cells in unphosphorylated form.

8. An isolated antibody that binds to the DP58 peptide wherein the epitope is SEQ ID NO: 4.

* * * * *